United States Patent
Altadonna, Jr.

(10) Patent No.: US 7,108,198 B2
(45) Date of Patent: Sep. 19, 2006

(54) NASAL AROMATHERAPY DISPENSER CLIP

(76) Inventor: James Altadonna, Jr., 203 Whitewood Dr., Massapequa, NY (US) 11762

( * ) Notice: Subject to any disclaimer, the term of this patent is extended or adjusted under 35 U.S.C. 154(b) by 0 days.

(21) Appl. No.: 10/280,682

(22) Filed: Oct. 25, 2002

(65) Prior Publication Data

US 2004/0079814 A1 Apr. 29, 2004

(51) Int. Cl.
- A24F 25/00 (2006.01)
- A61L 9/04 (2006.01)
- A61M 15/00 (2006.01)
- A61M 16/00 (2006.01)
- A61G 10/00 (2006.01)

(52) U.S. Cl. ............... 239/34; 128/200.24; 128/206.11
(58) Field of Classification Search .................. 239/34; 128/200.24, 206.11
See application file for complete search history.

(56) References Cited

U.S. PATENT DOCUMENTS

| | | | | |
|---|---|---|---|---|
| 1,579,486 A | * | 4/1926 | Pletcher | 128/203.22 |
| 3,463,149 A | * | 8/1969 | Albu | 128/204.12 |
| 3,905,335 A | * | 9/1975 | Kapp | 128/206.11 |
| 4,267,831 A | * | 5/1981 | Aguilar | 128/203.14 |
| 5,417,205 A | * | 5/1995 | Wang | 128/206.11 |
| 5,706,800 A | * | 1/1998 | Cronk et al. | 128/200.24 |
| 5,804,264 A | * | 9/1998 | Bowen | 428/35.2 |
| 6,015,425 A | * | 1/2000 | Altadonna, Jr. | 606/204.45 |
| 6,244,265 B1 | * | 6/2001 | Cronk et al. | 128/200.24 |
| 6,295,982 B1 | * | 10/2001 | Reed, Jr. | 128/200.24 |
| 2002/0153007 A1 | * | 10/2002 | Davi | 128/200.24 |

* cited by examiner

*Primary Examiner*—William C. Doerrler
(74) *Attorney, Agent, or Firm*—Alfred M. Walker

(57) ABSTRACT

An intra nasal dispenser clip for aromatherapy and for dispensing fragrances or aromatically odorous medicine includes a bendable arcuate band extending between distal ends. The ends have a pair of hollow aroma or aromatically odorous medicine dispensing containers, with hollow fragrant aroma dispensing containers affixed thereat. The hollow aroma or aromatically odorous medicine dispensing containers applying the fragrant or medically active aroma directly within the nostrils of the person using the clip. The band contacts the respective right and left sides of a user's nasal septum, with the band wrapped around the distal end of the nasal septum. The arcuate band is gentle on the nasal septum due to the geometry of the arcuate band being a wide circular arc bottom spring member, with inflection points at either distal ends, from which shorter reversed circular arcs emerge with the hollow aroma-dispensing containers at their distal ends.

33 Claims, 5 Drawing Sheets

NASAL AROMATHERAPY DISPENSER CLIP

FIELD OF THE INVENTION

The present invention relates to an intra-nasal clip for dispensing fragrances or odors, such as with used in aromatherapy, as well as for dispensing nasally administered aromatically odorous ingestable medicines.

BACKGROUND OF THE INVENTION

Aromatherapy is the traditional and scientific art and practice of using essential oils for the treatment of illness or to restore or enhance health, beauty, and well being. These essential oils are extracted from aromatic plants and herbs. Cedar Vale Company, an Internet supplier of essential oils (www.cedarvale.net) lists 177 such essential oils with therapeutic properties.

According to Dr. Kurt Schnaubelt, Director of the Pacific Institute of Aromatherapy, essential oils exert their therapeutic effect through pharmacological properties and small molecular size, which easily penetrate bodily tissues.

Although inhalation is the principal method of administration, using a few drops of essential oils on a handkerchief is not a well-controlled method of use. Furthermore, it is well known that several essential oils including anise, bitter almond, cedarwood, peppermint, sage, and wintergreen can be especially irritating to the skin.

While nasal clips are used in aromatherapy, most of the aromatherapy dispensers are "extra nasal" in that they deliver from outside the nostrils. For example, the "BREATHE RIGHT" strip, as described in U.S. Pat. Nos. 5,706,800 and 6,244,265, both of Cronk emits aromatherapy aromas, but only outside the nostrils.

The CNS "BREATHE RIGHT" strip bends around, and goes over the outside of, the nose, and emits fragrances therefrom in the vicinity of the nose. However, the CNS BREATHE RIGHT strip loses approximately 90% of the aromas to the air outside of the nose, where the aromas are emitted, not directly into the nostrils.

Among other patents for nasal administration of fragrances is U.S. Pat. No. 6,015,425 of the Applicant James Altadonna, Jr. herein describes a U-shaped nasal clip for delivering fragrances in malodorous environments, such as in a dental office or work site. As noted in Altadonna '425, dental patients often complain about foul odors associated with certain procedures. The source of the odor is generally acknowledged to be bacterial decay within the mouth due to high temperatures generated by the drilling of teeth. The present invention reduces or completely masks the unpleasant odors in a convenient and aggressive manner. However, in Altadonna '425, all of the spring force of the arcuate U-shaped band is directed at the inflection points of the opening points of the intra-nasal clip band against the nasal septum of the user.

Therefore, there is a need to provide an intra-nasal clip, which spreads out and deflects some of the impinging spring force of the intra-nasal clip away from where the nasal-clip impinges upon the nasal septum of the user.

Other nose clips are disclosed in U.S. Pat. No. Re. 35,408 of Petruson describes a resilient nasal clip that pushes outward against the nasal sidewalls to maximize the nostril openings, a feature not desired by the present invention.

Among other related patents include U.S. Pat. No. 6,325,475 of Hayes for a mechanical inhaler for aromatherapy, U.S. Pat. No. 6,399,192 of Pinna for a skin adhered patch with microcapsules, U.S. Pat. No. 3,655,129 of Seiner for slow release pads, U.S. Pat. No. 3,688,985 of Engel for making odor releasing pads, U.S. Pat. No. 3,994,439 of Van Breen for slow release air fresheners, U.S. Pat. No. 4,492,644 of Matsomoto for slow release perfumes, U.S. Pat. No. 4,808,466 of Kotani for deodorant sheets and U.S. Pat. No. 5,622,992 of Beck for aromatic products for nasal passage congestion.

Nasal administration and ingestion of medicines are also known, such as with inhalers administrating particles or nebulizers administering mists.

Among related patents for nasal administration of medicines include U.S. Pat. No. 6,051,244 of Perricone for nasal administration of a fructose diphosphate gel for treatment or preventing epidermal or mucosal aging and inflammation. U.S. Pat. No. 5,543,434 of Weg describes the nasal administration of a dry powder such as ketamine for treatment of pain. U.S. Pat. No. 6,391,340 of Malmqvist-Granlund describes nasal administration of dry powders for treating conditions of the nose, such as antihistamines, i.e., lotatidine and terfenadine, anti-inflammatories, i.e., steroids, anticholinergic agents, i.e. ipratropium bromide, thiotropium bromide, oxytropium bromide, and vasoconstrictors. Malmqvist-Granlund '340 also describes the nasal administration of dry powders for other classes of drugs, such as proteins, peptides such as insulin, hormones, etc., as well as mixtures of such drugs, and salts, sovates, hydrates and esters thereof. Moreover, Nastech Pharmaceutical Company, Inc. of New York, N.Y. produces nasally administered forms of apomorphine hydrochloride for sexual dysfunction, morphine gluconate as an opioid analgesic, scopalamine hydrobromide as an anti-motion sickness medicine, interferon alpha for treating cancer and hepatitis, interferon beta for treating relapsing forms of multiple sclerosis, somataropin for treating growth failure and triptans for treating migraine. In addition, nasal administered FLONASE® of GlaxoSmithKline, is a metered dose aqueous suspension of microfine fluticasone propionate for treating nasal inflammations. In addition, U.S. Pat. No. 6,342,478 of Frey describes nasal administration of fibroblast growth factors to the brain via the olfactory nerve for treating Alzheimer's disease.

However, the aforesaid nasal administrations of medicines are by direct contact from squirting or other pumping of the medicine directly into the nasal passage tissues, which may irritate nasal tissues.

Moreover, medicines may be delivered in aromatically odorous form, such as from a VAPORIZER® steam dispenser, but they require access to electricity and water, and restrict the mobility of the patient to the room in which the VAPORIZER® is located. Portable vaporizers are known, such as a mist inhaler described in U.S. Pat. No. 5,186,164 of Raghuprasad and U.S. Pat. No. 5,195,514 of Liu, but they still require mechanical and/or electrical components.

Other nose clips are known, but they are generally used to hold the nostrils closed, as in swimming or surgical procedures, as discussed in U.S. Pat. No. 4,231,360 of Zloczysti, and U.S. Pat. No. 4,445,508 of Lake.

To reduce malodorous mouth odors, various formulations in the form of tablets, liquids, or other medicaments are applied to the mucosol cavities of the user's mouth, such as disclosed in U.S. Pat. No. 4,303,648 of Witzel, U.S. Pat. No. 4,606,912 of Rudy, or U.S. Pat. No. 5,281,415 of Suzuki. But these cannot be applied during dental procedures, except by intermittent spraying or ingesting into the patient's mouth.

Furthermore, odor reducing filter masks are known, but these generally cover the whole face or the whole nose, 4s in U.S. Pat. No. 5,636,629 of Patterson for a filter mask Other odor reducing filter masks which cover the face or the nostrils of the nose include U.S. Pat. No. 5,392,773 of Bertrand and U.S. Pat. No. 5,740,798 of McKinney for filter masks that cover and mask the outer nostril end of the nose. Masks which cover the whole nose include U.S. Pat. No. 5,243,708 of Vanuch and U.S. Pat. No. 5,697,105 of White.

Moreover, U.S. Pat. No. 5,636,628 of Barnum discloses a mask to counteract odors that includes a cloth substrate covering the nose and mouth of the user, wherein the cloth substrate is held over the face by ear pieces which tie around the ears.

U.S. Pat. No. 5,538,013 of Brannon describes a mask with a scenting means. However, the mask of Brannon '013 covers at least the whole nose of the user.

In addition, U.S. Pat. No. 5,503,167 of Wilson et al. discloses a face shield covering the whole face of a user, wherein the user holds the face shield by gripping a mouthpiece between the user's teeth.

Furthermore, U.S. Pat. No. 4,267,831 of Aguilar and U.S. Pat. No. 5,417,205 of Wang describe nasal air filters and medicament dispenser devices, wherein two medication dispensing tubes are provided, one for insertion into each nostril. The problem with Aguilar '831 and Wang '205 is that the cylindrical outer surfaces of each tube completely block each nostril, thus increasing discomfort and preventing normal breathing through the nostrils.

However, these face coverings or nose covering masks are bulky and interfere with normal breathing during dental procedures.

OBJECTS OF THE INVENTION

It is therefore an object of the present invention to provide an intra-nasal clip for aromatherapy and nasal administration of aromatically odorous medicine, which can be inserted into the nasal passages.

It is another object of the present invention to provide a comfortable bendable arcuate band for aromatherapy having aroma-emitting dispensers affixed thereon, wherein only the aromas emitted therefrom contact the nasal tissues, not the source of the aromas.

It is yet another object of the present invention to provide an intra-nasal clip which spreads out and deflects some of the impinging spring force of the intra-nasal clip away from where the nasal-clip impinges upon the nasal septum of the user.

It is also an object provide a convenient odor emitting nasal clip which is compact and comfortable to wear, without interfering with normal breathing during dental procedures and during administration of aromatherapy aromas and nasally administered aromatically odorous medicines.

It is yet another object of the present invention to provide an odor emitting intra-nasal clip for contacting the respective right and left sides of a user's nasal septum during aromatherapy and in malodorous environments.

It is another object of the present invention to provide for an odor-emitting intra-nasal clip with ends which are separated from contact with the surface of the user's nasal septum.

It is another object of the present invention to provide a nasal clip having miniature aroma and odor-emitting dispensing containers with aromas, aromatically odorous medicines and odorants dispensed therefrom.

It is yet another object of the present invention to provide an assembly of aromatherapy and aromatically odorous medicine dispensing and odor-emitting nasal clips in a plurality of attached, user-detachable sealed packaging pouches, wherein a single nasal clip is enclosed within each packaging pouch.

It is yet another object of the present invention to provide sterile packaging pouches for aromatherapy and aromatically odorous medicine dispensing and odor-emitting nasal clips with an odor and oxygen barrier.

It is another object of the present invention to provide packaging pouches for odor-emitting nasal clips with which can be torn off individually.

It is a further object of the present invention to alter a person's exposure to foul odors during a dental procedure or malodorous work environment.

It is yet another object of the present invention to provide an aromatherapy and aromatically odorous medicine dispensing and odor-emitting nasal clip with a pleasant-smelling odorant or aromatically odorous medicine.

It is yet another object of the present invention to improve over the disadvantages of the prior art.

SUMMARY OF THE INVENTION

In keeping with these objects and others which may become apparent, the present invention provides an aromatherapy and aromatically odorous medicine dispensing intra-nasal clip, as well as an odor desensitizing intra-nasal clip, for persons and which includes a bendable arcuate band extending between its outer distal ends, wherein the ends having aromatherapy, aromatically odorous medicine and odor-emitting dispensers affixed thereon.

The band has an inner surface which is coextensive with the band. The inner surface contacts the respective right and left sides of a user's nasal septum when the distal ends of the nasal clip are inserted into a user's right and left nostrils, with the band wrapped around the distal end of the dental patient's nasal septum.

The nasal aromatherapy and aromatically odorous medicine dispenser clip of this invention is uniquely designed to be easy to attach to the nasal septum. It is comfortable to use and places aroma and aromatically odorous dispensing material within hollow containers at the distal ends of an arcuate band. The aroma dispensing material within the hollow containers emit a controlled release of vapors from essential oils within each nostril. The placement of the essential oils within the hollow containers of the intra-nasal clip also protects the sensitive mucous membranes from direct physical contact with the essential oils.

The essential oils and aromatically odorous medicines dispensed from the intra-nasal clip can be used directly in liquid form within the hollow aroma dispensing containers at the distal ends of the intra-nasal clip. However to prevent spillage from the open top of each hollow container, an absorbent fabric or foam pad can be used within each of the two hollow aroma and aromatically odorous medicines dispensing containers.

An alternative method is to use a permeable liquid-phobic membrane seal to seal the open top of each container with the liquid essential oil and aromatically odorous medicines within.

Although methods of formulating controlled release granules or powders from the essential oils are not part of this invention, such compositions can be used within each of the containers and then sealed with a micro-screen or permeable membrane at the open top to prevent spillage. Using the methods described in Van Breen et al. (U.S. Pat. No. 3,994,439), Matsumoto et al. (U.S. Pat. No. 4,492,644), or Seiner (U.S. Pat. No. 3,655,129), essential oils can be formulated into slow-release solid compositions which are then inserted into the containers of nasal aromatherapy and aromatically odorous medicine dispenser clip of this invention.

Whichever formulation of essential oil or method of sustained release is used, the open top of each container of the nasal clip is sealed (atop a permeable membrane or screen if used) with a small strip of impermeable tape which must be removed just prior to use. This will insure a long shelf life.

The dispenser clip is preferably molded of a thermoplastic resin such as polyvinyl chloride (PVC), polycarbonate, ABS, or a number of other non-irritating plastic resins with a suitable modulus of elasticity and essential oil compatibility.

The preferred embodiment uses an arcuate band having a geometry which minimizes spring pressure at its attachment points with the user's nasal septum. For example, the arcuate band of the intra-nasal clip is an arcuate bottom spring member with inflection points at either distal ends, from which shorter reversed circular arcs emerge, with small rectangular hollow aroma dispensing containers at their distal ends. This geometric design easily expands to fit over the bulbous end of the nasal septum while staying in place thereafter with minimal spring force, if any, impinging on the sides of the nasal septum. An alternate embodiment using oval containers and a different geometry for clipping onto the nasal septum is also described.

The band also preferably includes a pair of reverse curvatures near its outer distal ends. The reverse curvatures separate the ends from contact with the surface of the user's nasal septum.

The intra-nasal clip has odor-emitting containers, such as a pair of hollow aroma and aromatically odorous medicine dispensing containers attached to the outer distal ends of the nasal clip, with pleasant smelling odorant or aromatically odorous medicine absorbed therewithin in liquid, powder or gel form. A screen or permeable membrane preferably covers the containers. Solid time-release techniques can be used as well.

The intra-nasal clip is flexible, spring-like and semi-rigid, and is made of a flexible spring-like and semi-rigid material, such as aluminum or plastic.

The nasal clip should be preferably packaged in a sterile environment, such as in a plurality of attached, user-detachable sealed packaging pouches wherein a single nasal clip is enclosed within each packaging pouch. To retain freshness, each packaging pouch includes an odor and oxygen barrier.

To remove a packaged nasal clip, each packaging pouch has a weakening seam for facilitating user tear-off of individual packaging pouches as desired, such as perforations between each packaging pouch.

Furthermore, the odor emitting nasal clip of the present invention alters dental patient's exposure to foul odors during a dental procedure, by masking dental bacterial odors. The nasal clips are used by inserting each end into a respective nostril of the user, wherein the nasal clip is held in place within the nostrils of the user, by clamping against the nasal septum.

Therefore, the present invention includes a miniature air freshener designed to be attached to the distal end of the nasal septum. It applies a pleasant scent, an aromatherapy fragrance or aromatically odorous medicine directly within the nostrils.

Such a convenient, inexpensive, and effective personal air freshener can have other applications besides the dental usage described above. There are several situations which expose practitioners to environments with intense vile odors. Examples of such occupational hazards include crime scene investigations, autopsies of decaying cadavers, and work associated with sewage systems.

The benefits of the present invention are as follows:

1) providing aromas directly within the nose maximizes the amount of aromas absorbed by the nasal passages of the user, as opposed to the reduced amount of aromas absorbed in the nasal passages when using the CNS "BREATHE RIGHT" strip, which loses approximately 90% of the aromas to the air outside of the nose, where the aromas are emitted;

2) up to now, fragrant aromas or aromatically odorous medicines have not been administered on a time release basis (i.e. nasal squirts are administered in a "one-shot" dosage administration);

3) the invention solves an unrecognized problem of maximizing aromatherapy and aromatically odorous medicine administration within the sensitive nasal passages of the user;

4) Other extra-nasal clips would not work within a nose;

5) the device solves a long felt need in aromatherapy and dispensing of and aromatically odorous medicine;

6) the whole is synergistic, i.e. the results of the use of the nasal clip and the method of administering aromas and aromatically odorous medicine with the nasal clip are greater than would be expected with other aromatherapy or aromatically odorous medicine dispensers.

BRIEF DESCRIPTION OF THE DRAWINGS

The present invention can best be understood in connection with the accompanying drawing, in which.

DETAILED DESCRIPTION OF THE PREFERRED EMBODIMENTS

Figure 1:
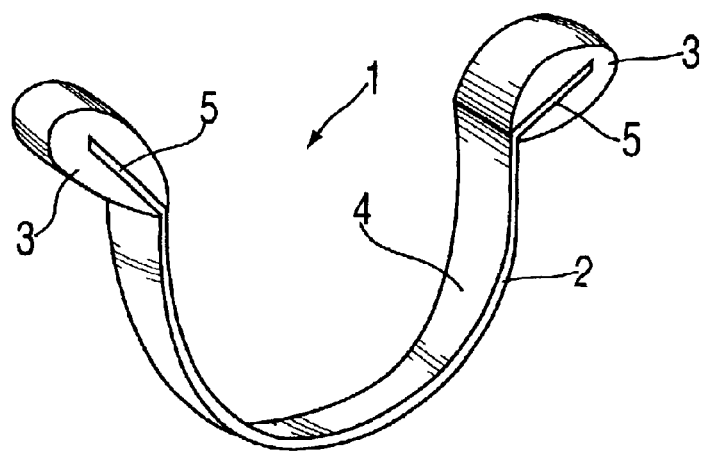
FIG. 1 is a perspective view of a prior art nasal air freshener.

FIG. 1 shows prior art nasal air freshener 1 which includes bendable frame 2 with distal frame ends 5 covered with absorbent pads 3. Inside surface 4 of frame 2 contacts the distal end of the nasal septum.

Figure 2:
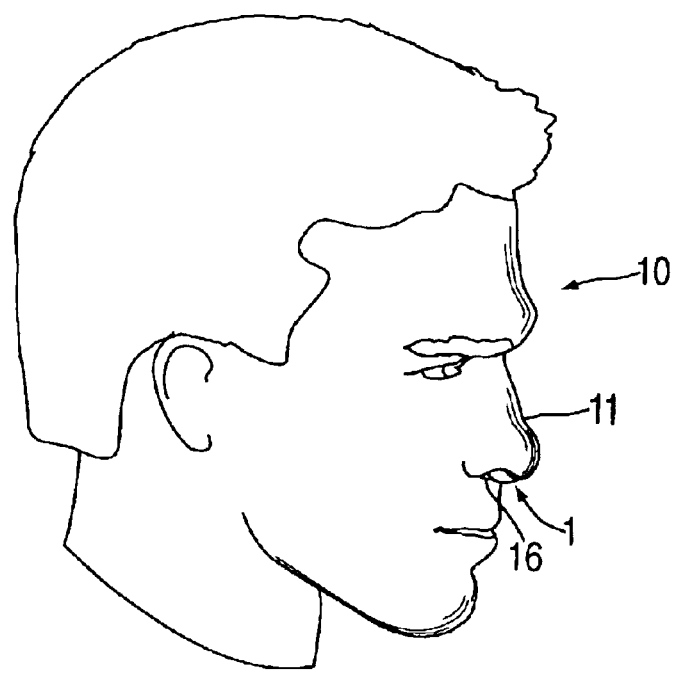
FIG. 2 is a side view of a facial profile of a user with prior art air freshener of the FIG. 1 in use.

When worn, (as shown in FIG. 2) prior art nasal air freshener 1 is hardly visible, as shown worn by user 10 within nose 11. More importantly, nasal air freshener 1 does not protrude from the end of nose 11. This is important especially for dental procedures requiring the use of a cotton roll under the upper lip, since any protrusions of nasal filter coverings as in the prior art would interfere with the dentist's procedures and be uncomfortable for the patient.

Figure 3:
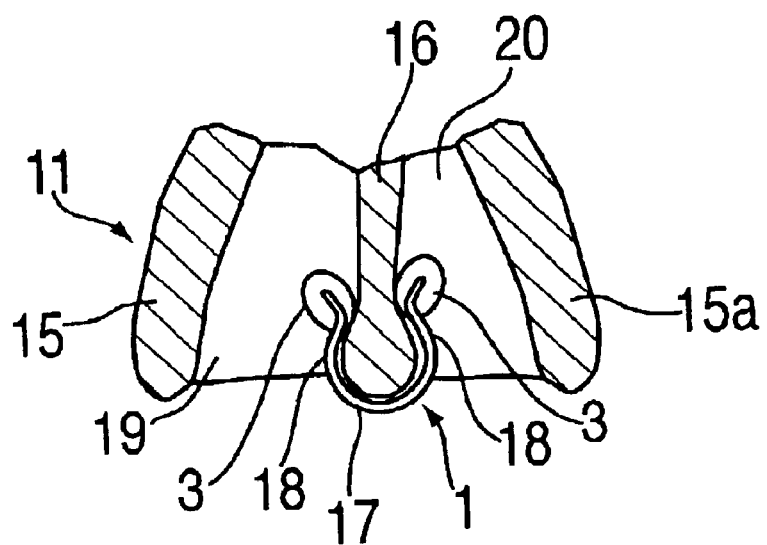
FIG. 3 is a front cross section detail of nasal passages showing the installation of the prior art nasal air freshener of FIG. 1.
Figure 4:
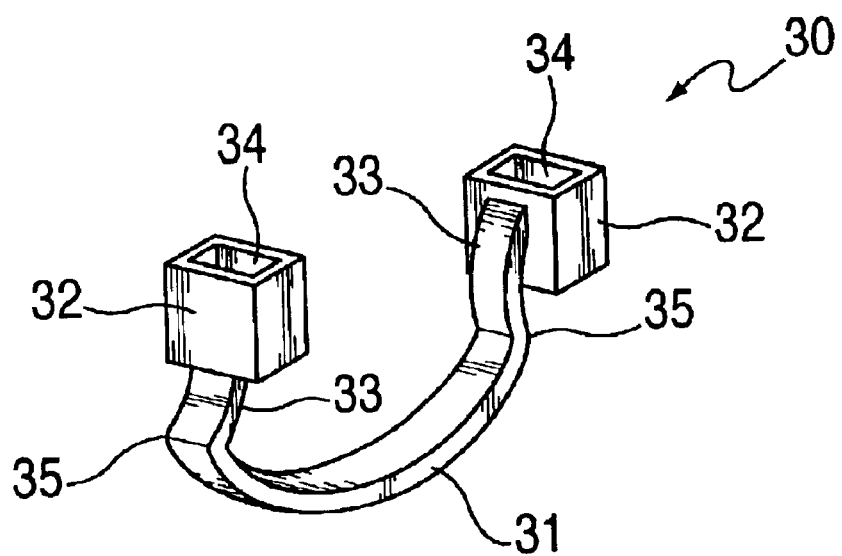
FIG. 4 is a perspective view of the preferred embodiment of the nasal aromatherapy dispenser clip of this invention.

FIG. 3 is a cross sectional detail view showing the internal nasal passages with prior art nasal air freshener 1 in place. Open nostrils 19 and 20 are formed between outer sides 15, 15a of nose 11 and nasal septum 16. Distal end 17 of nasal septum 16 is somewhat bulbous. Sides, 2a, 2b of frame 2 of nasal air freshener 1 are pressed together by the user so that they form neck 18, bending around end 17 of nasal septum 16 to retain nasal air freshener 1 in place.

Absorbent pads 3 are prominently positioned within the air flow within open nostrils 19 and 20 without significantly blocking these passages.

Aromatherapy and dispensing of aromatically odorous medicines is useful with the intra-nasal clip shown in FIGS. 4–11 of the present invention, because the chemical makeup of essential oils and aromatically odorous medicines gives them a broad range of pharmacological properties covering antibacterial, antiviral, and antispasmodic uses as well as diuretics, vasodilators and vasoconstrictors.

By interacting with the top of the nasal cavity, aromatically odorous molecules give off signals that are modified by various biological processes before travelling to the limbic system which is related to the emotional interactions of the brain.

Essential oils can therefore affect heart rate, blood pressure, breathing, memory, stress levels, and hormone balance. Immune response, moods and emotions and the ability to pacify, energize and detoxify are other aspects that can be affected by aromatherapy.

Findings have shown that orange, jasmine, and rose have a tranquilizing effect while the "stimulating" oils—basil, black pepper, and rosemary—can produce a heightened energy response.

If aromatherapy is to be more generally studied and prescribed, a method of application wherein convenient sustained release of essential oil vapors at a known controlled rate is essential.

In addition, aromatically odorous medicines in pharmacologically acceptable carriers may be delivered as aromas derived from the positioning of these medicines in gel, liquid or dry powder form within the dispensers of the nasal clip of the present invention. Such medicines may be provided in time release and body-weight calibrated dosages for absorption through the nasal passages of the wearer of the nasal clip.

Another requirement is to prevent contact with the liquid oil which may irritate the skin (especially sensitive nasal mucous membranes). The nasal aromatherapy and aromatically odorous medicine dispenser clip of this invention makes this possible.

FIGS. 4 through 7 therefore show various views of the preferred embodiment of nasal aromatherapy and aromatically odorous medicine dispensing clip 30. Molded of a plastic resin, it can be appreciated that bottom circular arc member 31 will act as a spring member and will deform elastically if a force is applied at X (see FIG. 5). At inflection points 35, reverse circular arc members 33 extend upwards terminating in essential oil containers 32 with open ends 34. Their internal volume is of the order of six cubic millimeters.

Figure 8:
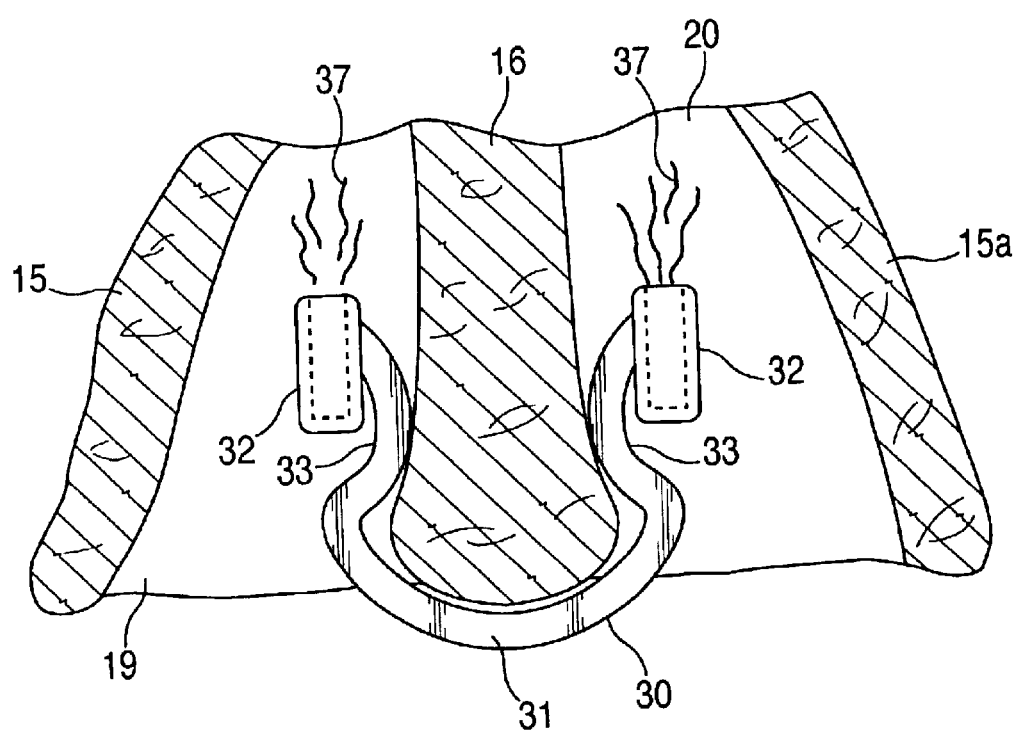
FIG. 8 is a front cross section detail of nasal passages showing the installation of the nasal aromatherapy dispenser clip.

By referring to FIG. 8, the fit of clip 30 on nasal septum 16 within nasal cavities 19 and 20 is revealed. FIG. 8 shows that the essential oil vapors and aromatically odorous medicines 37 are released right in the nasal cavities with no waste whatsoever. Containers 32 prevent any direct contact of essential oils and aromatically odorous medicines with mucous membranes.

Figure 6:
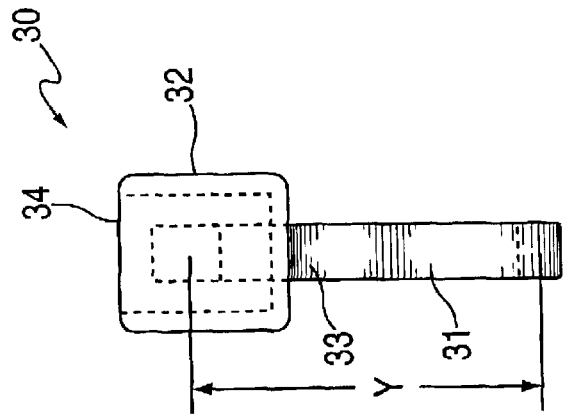
FIG. 6 is an end view of the dispenser clip thereof.
Figure 7:
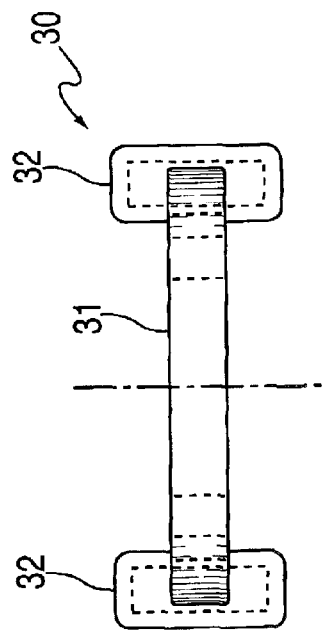
FIG. 7 is a bottom view of the dispenser clip thereof.
Figure 5:
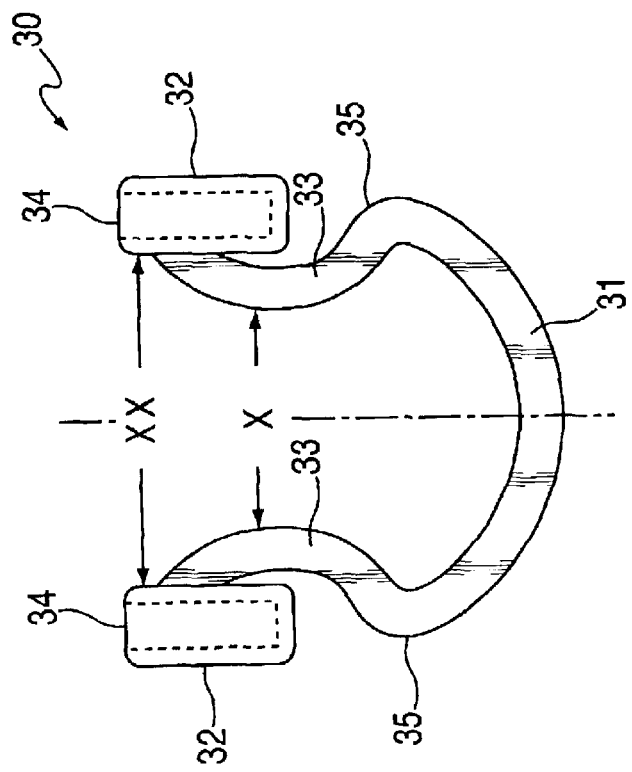
FIG. 5 is a side elevation of the dispenser clip as in FIG. 4.

Referring to FIGS. 5 and 6, it is shown that dimension X is only marginally less than the width of nasal septum 16 at the point of contact. Also, dimension XX is somewhat wider than the widest part of the bulbous distal end of septum 16. This insures easy entry of clip 30 onto nasal septum 16. Long dimension Y insures that the mechanical advantage as applied to spreading open spring member 31 by nasal septum 16 during installation will cause no discomfort.

Furthermore, the gently sloping contact surfaces of circular arcs 33 on nasal septum 16 adaptively conform to increase contact surface area as horizontal spring force is increased in cases where a user has an inflamed or normally wider septum; thus the pressure on the side of the septum is always kept at a minimal level.

Figure 10:
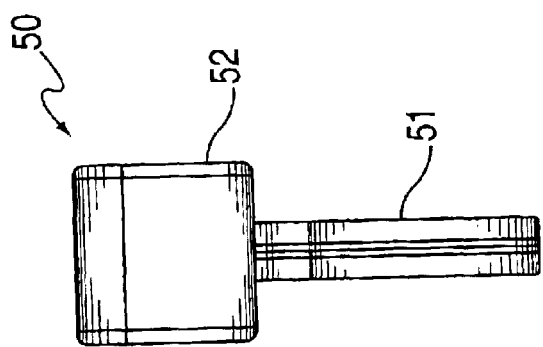
FIG. 10 is an end view of the alternate embodiment clip.
Figure 9:
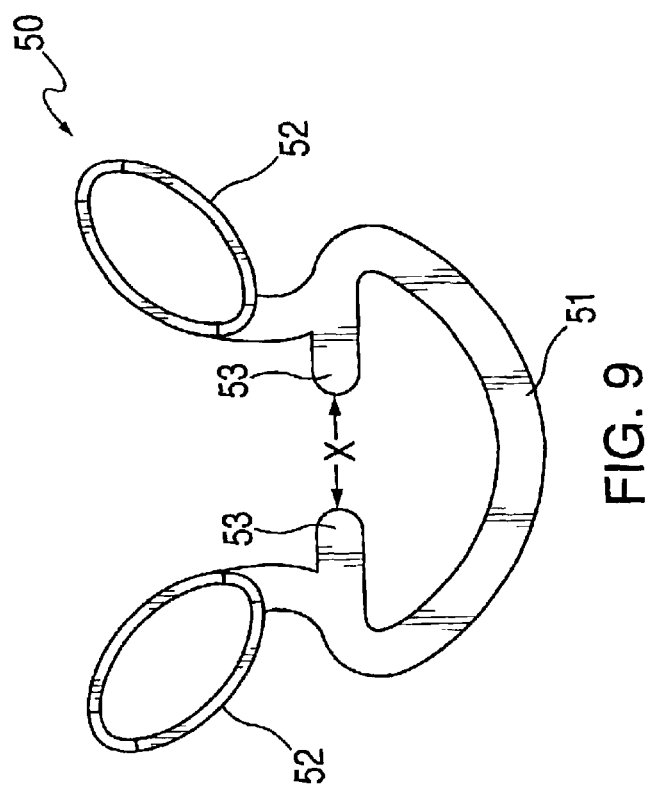
FIG. 9 is a side view of an alternate embodiment of the nasal aromatherapy dispenser clip.
Figure 11:
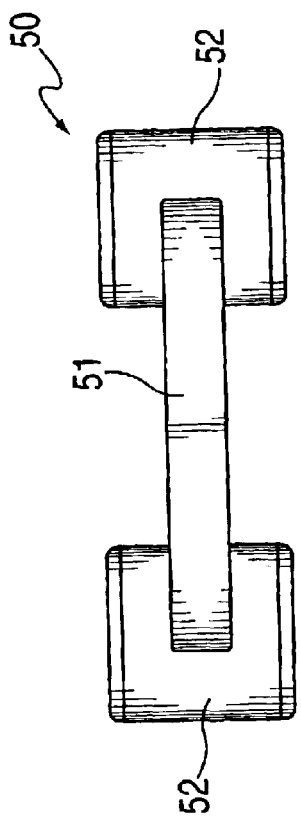
FIG. 11 is a bottom view of the alternate embodiment clip.

FIGS. 9–11 show three views of an alternate embodiment 50 of a nasal aromatherapy and aromatically odorous medicine dispenser clip. Here, hollow aroma and aromatically odorous medicine dispensing containers 52 are oval cylinders angled so as to facilitate easy placement over septum 16 during insertion. Dimension X between nibs 53 insures a comfortable fit over nasal septum 16 at the point of contact.

It is further noted that other modifications may be made to the present invention, without departing from the scope of the invention, as noted in the appended claims.

I claim:

1. An intra nasal dispenser clip comprising:
    a bendable arcuate band extending between distal ends, said ends having a pair of hollow aroma dispensing containers, each said hollow aroma dispensing container comprising fragrant odor emitting means affixed thereon applying said fragrant odor directly within the nostrils of the person;
    said band having a inner surface coextensive with said band, said inner surface for intra-nasal contacting the respective right and left sides of a user's nasal septum, when said distal ends are inserted into a user's right and left nostrils with said band wrapped around the distal end of the nasal septum;
    said band having a pair of inflected reverse curvatures near said respective distal ends, said reverse curvatures providing for separation of said ends from contact with the surface of the user's nasal septum; and,
    said band being a wide bowed circular arc bottom spring member with inflection points at either distal ends of said wide bowed circular arc bottom spring member from which shorter reversed circular arcs emerge with said hollow aroma dispensing containers at their distal ends.

2. The intra nasal dispenser clip a in claim 1 wherein said nasal clip dispenses a fragrance.

3. The intra nasal dispenser clip a in claim 1 wherein said nasal clip dispenses an aromatherapy aroma.

4. The intra nasal dispenser clip a in claim 1 wherein said nasal clip dispenses an aromatically odorous medicine.

5. The intra nasal dispenser clip a in claim 1 wherein said ends of said nasal clip comprise respective hollow aroma dispensing containers housing material which emits a controlled release of vapors from essential oils within each nostril of the user.

6. The intra nasal dispenser clip a in claim 5 wherein said respective hollow aroma dispensing containers of said nasal clip isolate and protect a sensitive mucous membranes from contact with the essential oils contained within said hollow aroma dispensing containers.

7. The intra nasal dispenser clip as in claim 5 wherein said essential oils are in liquid form within said hollow aroma dispensing containers.

8. The intra nasal dispenser clip as in claim 5 wherein to prevent spillage form the open top, an absorbent aroma emitting pad is provided within each of said hollow aroma dispensing containers.

9. The intra nasal dispenser clip as in claim 5 wherein a permeable liquid-phobic membrane seals said open top of each said hollow aroma dispensing container having said liquid essential oil therewith.

10. The intra nasal dispenser clip as in claim 1 wherein controlled release essential oil compositions are provided within each of said containers and then sealed with a micro-screen membrane at said open tops of each of said hollow aroma dispensing containers to prevent spillage therefrom.

11. The intra nasal dispenser clip as in claim 1 wherein each said open top of each said hollow aroma dispensing container of said nasal clip is sealed with a removable strip of impermeable material.

12. The intra nasal dispenser clip as in claim 1 wherein said intra nasal dispenser clip is molded of a material selected from the group consisting of thermoplastic resins, polyvinyl chloride (PVC), polycarbonate and ABS.

13. The intra nasal clip as in claim 1 wherein said intra nasal clip comprises a plurality of intra nasal clips contained within a plurality of attached, user-detachable sealed packaging pouches wherein a respective single unit of said clip is enclosed within each respective packaging pouch.

14. The clip of claim 13 wherein said packaging pouches comprise an odor and oxygen barrier.

15. The clip of claim 13 wherein said respective packaging pouches have weakening means for facilitating user tear-off of individual packaging pouches as desired.

16. The clip of claim 13 wherein said weakening means comprises perforations between respective packaging pouches.

17. a method of exposing a person to a fragrant odor comprising the steps of:
   a. affixing hollow aroma dispensing containers to the ends of a soft, bendable arcuate band having two ends and a reverse curvature near each respective end, said arcuate band being a wide bowed circular arc bottom spring member with inflection points at either distal ends of said wide bowed circular arc bottom spring member from which shorter reversed circular arcs emerge with said hollow aroma dispensing containers at their distal ends;
   b. filling said hollow aroma dispensing containers with a pleasant-smelling odorant;
   c. packaging said arcuate band in a sealed pouch having an odor and oxygen barrier;
   d. opening said pouch at the beginning of a procedure at the malodorous location;
   e. inserting said ends of said band into the nostrils of the user;
   f. wrapping said band around the end of the user's nose;
   g. gently pressing said band into contact with the right and left sides of the inner nasal septum of the user, for grasping contact therebetween;
   h. ensuring that said reverse curvatures near said ends cause separation between the surface of the user's nasal septum and said hollow fragrance emitting containers; and,
   i. removing said clip at the end of the procedure sooner if desired.

18. An intra nasal dispenser clip comprising:
   a bendable arcuate band extending between distal ends, said ends having a pair of hollow aroma dispensing containers, each said hollow aroma dispensing container comprising fragrant odor emitting means affixed thereon applying said fragrant odor directly within the nostrils of the person;
   said band having a inner surface coextensive with said band, said inner surface for intra-nasal contacting the respective right and left sides of a user's nasal septum, when said distal ends are inserted into a user's right and left nostrils with said band wrapped around the distal end of the nasal septum;
   said band having a pair of inflected reverse curvatures near said respective distal ends, said reverse curvatures providing for separation of said ends from contact with the surface of the user's nasal septum; and,
   said band being a wide bowed circular arc bottom spring member with angular inflection points at either distal ends of said wide bowed circular arc bottom spring member from which shorter reversed circular arcs emerge with said hollow aroma dispensing containers at their distal ends.

19. The intra nasal dispenser clip as in claim 18 wherein said nasal clip dispenses a fragrance.

20. The intra nasal dispenser clip as in claim 18 wherein said nasal clip dispenses an aromatherapy aroma.

21. The intra nasal dispenser clip as in claim 18 wherein said nasal clip dispenses an aromatically odorous medicine.

22. The intra nasal dispenser clip as in claim 18 wherein said ends of said nasal clip comprise respective hollow aroma dispensing containers housing material which emits a controlled release of vapors from essential oils within each nostril of the user.

23. The intra nasal dispenser clip as in claim 22 wherein said respective hollow aroma dispensing containers of said nasal clip isolate and protect sensitive mucous membranes from contact with the essential oils contained within said hollow aroma dispensing containers.

24. The intra nasal dispenser clip as in claim 22 wherein said essential oils are in liquid form within said hollow aroma dispensing containers.

25. The intra nasal dispenser clip as in claim 22 wherein to prevent spillage from the open top, an absorbent aroma emitting pad is provided within each of said hollow aroma dispensing containers.

26. The intra nasal dispenser clip as in claim 22 wherein a permeable liquid-phobic membrane seals said open top of each said hollow aroma dispensing container having said liquid essential oil therewith.

27. The intra nasal dispenser clip as in claim 18 wherein controlled release essential oil compositions are provided within each of said containers and then sealed with a micro-screen membrane at said open tops of each of said hollow aroma dispensing containers to prevent spillage therefrom.

28. The intra nasal dispenser clip as in claim 18 wherein each said open top of each said hollow aroma dispensing container of said nasal clip is sealed with a removable strip of impermeable material.

29. The intra nasal dispenser clip as in claim 18 wherein said intra nasal dispenser clip is molded of a material selected from the group consisting of thermoplastic resins, polyvinyl chloride (PVC), polycarbonate and ABS.

30. The intra nasal clip as in claim 18 wherein said intra nasal clip comprises a plurality of intra nasal clips contained within a plurality of attached, user-detachable sealed packaging pouches wherein a respective single unit of slid clip is enclosed within each respective packaging pouch.

31. The clip of claim 30 wherein said packaging pouches comprise odor and oxygen barrier.

32. The clip of claim 30 wherein said respective packaging pouches have weakening means for facilitating user tear-off of individual packaging pouches as desired.

33. The clip of claim 30 wherein said weakening means comprises perforations between respective packaging pouches.

* * * * *